(12) United States Patent
Mihalache

(10) Patent No.: US 9,184,673 B2
(45) Date of Patent: Nov. 10, 2015

(54) PULSE WIDTH MODULATION CONTROL FOR A MULTILEVEL CONVERTER

(71) Applicant: SIEMENS INDUSTRY, INC., Alpharetta, GA (US)

(72) Inventor: Liviu Mihalache, Evans City, PA (US)

(73) Assignee: SIEMENS AKTIENGESELLSCHAFT, München (DE)

(*) Notice: Subject to any disclaimer, the term of this patent is extended or adjusted under 35 U.S.C. 154(b) by 71 days.

(21) Appl. No.: 14/206,019

(22) Filed: Mar. 12, 2014

(65) Prior Publication Data
US 2015/0263645 A1    Sep. 17, 2015

(51) Int. Cl.
| | | |
|---|---|---|
| H02P 1/00 | (2006.01) |
| H02P 1/28 | (2006.01) |
| H02P 3/00 | (2006.01) |
| H02P 7/06 | (2006.01) |
| H02P 7/14 | (2006.01) |
| H02P 23/00 | (2006.01) |
| H02P 25/00 | (2006.01) |
| H02P 27/00 | (2006.01) |
| H02M 7/537 | (2006.01) |
| H02P 27/14 | (2006.01) |
| A61B 17/16 | (2006.01) |
| B26B 19/06 | (2006.01) |
| B26B 19/00 | (2006.01) |

(52) U.S. Cl.
CPC ............... *H02M 7/537* (2013.01); *H02P 27/14* (2013.01); *A61B 17/1626* (2013.01); *B26B 19/00* (2013.01); *B26B 19/06* (2013.01)

(58) Field of Classification Search
CPC .... A61B 17/1626; B26B 19/00; B26B 19/06; B26B 19/38; B26B 19/388
USPC ......................................................... 318/504
See application file for complete search history.

(56) References Cited

U.S. PATENT DOCUMENTS 5,625,545 A * 4/1997 Hammond ...................... 363/71
6,166,513 A * 12/2000 Hammond .................... 318/764

(Continued)

OTHER PUBLICATIONS

Brendan Pter McGrath, Guillaume Gateau and Donald Grahame Holmes, "Optimal Modulation of Flying Capacitor and Stacked Multicell Converters Using a State Machine Decoder", IEEE Transactions on Power Electronics, vol. 22, No. 2, Mar. 2007, pp. 508-516.

(Continued)

*Primary Examiner* — Kawing Chan
*Assistant Examiner* — Bradley Brown

(57) ABSTRACT

A method for controlling a switching device of a multilevel converter includes dynamically selecting a carrier and generating a switching signal to effect a switching event of the switching device based on a comparison of the dynamically selected carrier with a reference signal. The carrier is dynamically selected from a multiple carriers, each corresponding to one of multiple contiguous bands into which range of a waveform of the reference signal is divided. The carriers corresponding to different bands have differing waveform shapes. The dynamically selected carrier corresponds to the band instantaneously occupied by the reference signal. The dynamic selection is executed whereby whenever there is a transition of the reference signal from a first band to a second band, the carriers for the first and second bands are selected dependent on a slope of the reference signal waveform at the transition.

20 Claims, 13 Drawing Sheets

(56) References Cited

U.S. PATENT DOCUMENTS

| | | | | |
|---|---|---|---|---|
| 6,301,130 | B1* | 10/2001 | Aiello et al. | 363/37 |
| 2002/0085398 | A1* | 7/2002 | Bixel | 363/41 |
| 2003/0231517 | A1* | 12/2003 | Bixel | 363/71 |
| 2007/0058405 | A1* | 3/2007 | Bousfield et al. | 363/132 |
| 2011/0002149 | A1 | 1/2011 | Hiller et al. | |
| 2013/0286704 | A1* | 10/2013 | Liu et al. | 363/132 |

OTHER PUBLICATIONS

Dae-Wook Kang, Yo-Han Lee, Bum-Seok Suh, Chang-Ho Choi and Dong-Seok Hyun, "An Improved Carrier-Based SVPWM Method Using Leg Voltage Redundancies in Generalized Cascaded Multi-level Inverter Topology", IEEE Transactions on Power Electronics, vol. 18, No. 1, Jan. 2003, pp. 180-187.

* cited by examiner

PULSE WIDTH MODULATION CONTROL FOR A MULTILEVEL CONVERTER

BACKGROUND

1. Field

Aspects of the present invention relate to a multilevel power converter, particularly to pulse width modulation control of a multilevel converter.

2. Description of the Related Art

Traditionally, multilevel power converters are used in the applications of medium voltage AC drives, flexible AC transmission systems (FACTS), and High Voltage DC (HVDC) transmission systems, because single power semiconductor devices cannot handle high voltage. Multilevel converters typically include a plurality of power cells for each phase, each power cell including an inverter circuit having semiconductor switches that are capable of altering the voltage states or levels of the individual cells. Depending on the type of inverter circuitry used (for e.g., half-bridge or full bridge), each power cell may have one or more switching legs. By controlling the switching events of the individual switching legs of each power cell, it is possible to control the voltage across each cell and resultantly obtain an AC output waveform having multiple discrete voltage levels. A multilevel converter is often described by the number of discrete levels in output voltage waveform.

In certain applications, it may be desirable to control the switching events in a multilevel converter using Pulse Width Modulation (PWM). A PWM based control provides several benefits, especially a reduction in the harmonic spectrum at every level. Multilevel converters typically use phase-shifted triangular carriers at the heart of the PWM method. A conventional method used for multilevel converters, particularly those having a cascaded H-bridge topology, is phase-shifted pulse width modulation (PS-PWM) carrier method. In the PS-PWM method, a reference signal for a particular cell, which is typically a sine-waveform, is compared against a triangular carrier in order to obtain the switching instances for a first switching leg of the cell. Each cell has its own triangular carrier. In the PS-PWM method these carriers are phase-shifted. The same reference sine-waveform is compared against the inverted triangular carrier in order to obtain the switching instances for the second switching leg of the same cell.

But the conventional methods, such as those mentioned above, do not provide an optimum spectrum for the line-line output voltage. The quality of the output voltage deteriorates especially at high output voltage frequency, or when the converter has a low number of levels. Typically if the output voltage frequency is high and the converter has a reduced number of levels, an obvious option is to increase the switching frequency. But increasing the switching frequency also increases the overall losses.

SUMMARY

Briefly, aspects of the present invention relate to a multilevel power converter. Aspects of the present invention also relate to pulse width modulation control of a multilevel converter.

A first aspect of the invention provides a method for controlling a switching device of a multilevel converter. The method includes dynamically selecting a carrier signal, and generating a pulse width modulation (PWM) signal to effect a switching event of the switching device based on a comparison of the dynamically selected carrier signal with a reference signal. The carrier signal is dynamically selected from a plurality of carrier signals. Each of the plurality of carrier signals can correspond to one of a plurality of contiguous bands that fully occupy a range of a waveform of the reference signal. The carrier signals corresponding to different bands have differing waveform shapes. The dynamically selected carrier signal can correspond to a band that is instantaneously occupied by the reference signal. The dynamic selection is carried out whereby whenever there is a transition of the reference signal from a first band to a second band, the carrier signals selected for the first band and the second band are dependent on a slope of the waveform of the reference signal at the transition.

A second aspect of the invention provides a multilevel converter for producing a multiphase AC power supply. The multilevel converter includes a plurality of power cells for supplying power to each phase, each power cell comprising at least one switching leg incorporating a semiconductor switch. The multilevel converter further includes a PWM controller connected to each of the power cells for controlling the voltage output of the respective power cells by controlling a switching event of each of the switching legs. The PWM controller dynamically selects a carrier for an individual switching leg and generates a switching signal to effect a switching event for the individual switching leg based on a comparison of the dynamically selected carrier with a reference signal. The PWM controller executes the dynamic selection of the carrier for the individual switching leg from a plurality of carriers. Each of the plurality of carriers can correspond to one of a plurality of contiguous bands that fully occupy a range of a waveform of the reference signal. The carriers corresponding to different bands have differing waveform shapes. The dynamically selected carrier can correspond to the band that is instantaneously occupied by the reference signal. The dynamic selection is executed whereby whenever there is a transition of the reference signal from a first band to a second band, the carrier signals selected for the first band and the second band are dependent on a slope of the waveform of the reference signal at the transition.

DETAILED DESCRIPTION

Embodiments of the present invention relate to a new pulse width modulation (PWM) method which can be, in principle, used for many different types of multilevel converters. In general, a multilevel converter may have one or more phases, including a plurality power cells for each phase. Each power cell includes an inverter circuit having one or more switching legs provided with switching devices, which are capable of altering the voltage states or levels of the individual cells. By controlling the switching events of the individual switching legs of each power cell, it is possible to control the voltage across each cell and resultantly obtain an AC output waveform having multiple discrete voltage levels.

While the embodiments of the present invention have been illustrated for certain exemplary multilevel converters that can be used in industrial applications, it is to be understood that the proposed PWM controller and its underlying methods of operation are not limited to the herein described types of multilevel converters, but can be generalized for multilevel converters with any number of cells or to many other multilevel topologies.

Example 1

Cascaded H-Bridge Multilevel Converter

In a first embodiment, a proposed modulation method is illustrated for a cascaded H-bridge multilevel converter. An example of such a converter is the Perfect Harmony GH180® drive manufactured by Siemens Industry, Inc.

Figure 1:
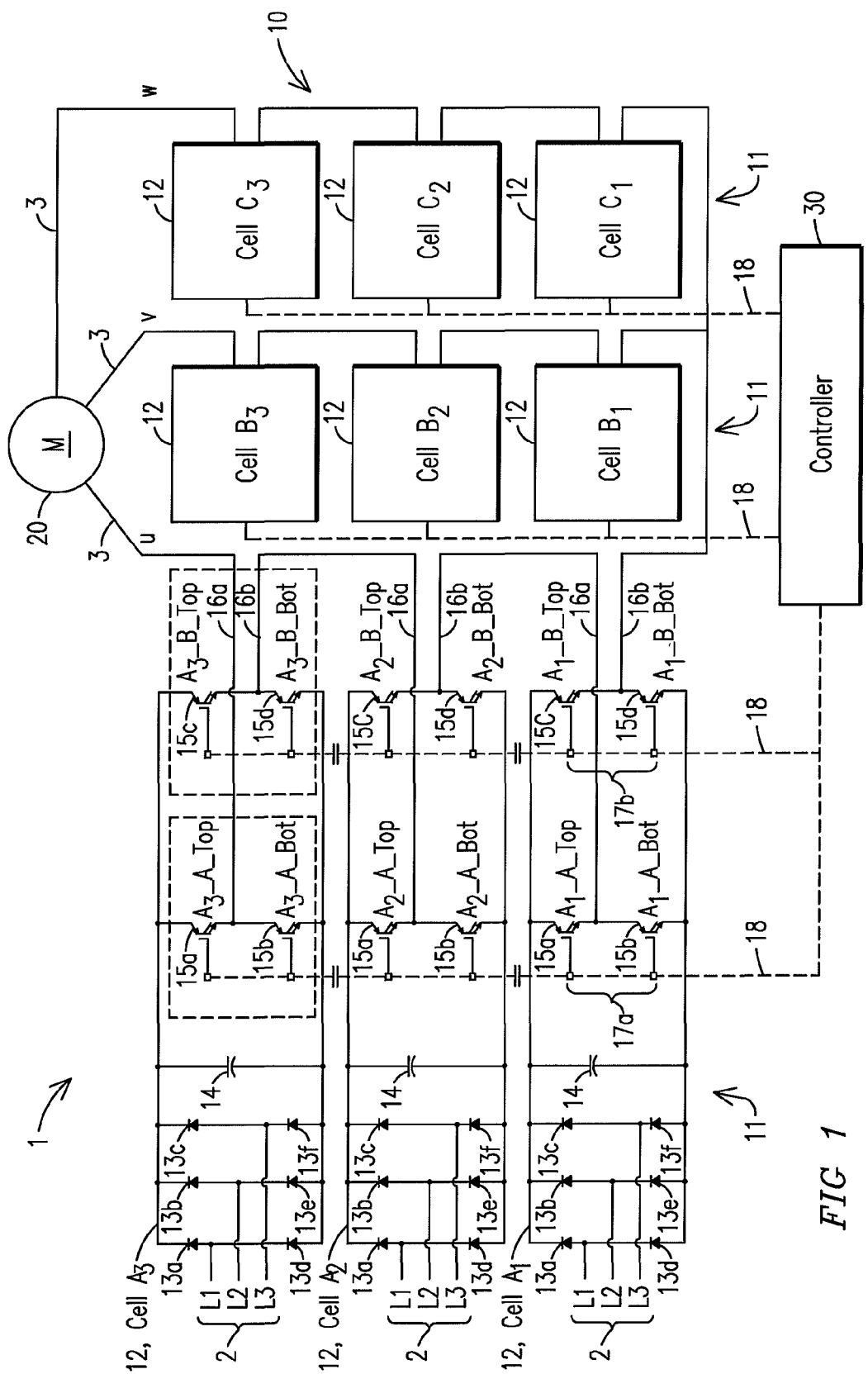
FIG. 1 is a schematic diagram illustrating a cascaded three-phase H-bridge multilevel converter having three cells/phase topology in accordance with a first example embodiment.

FIG. 1 illustrates a schematic of an embodiment of a system 1 comprising cascaded H-bridge multilevel converter 10 having a seven-level topology, including three phases with three power cells per phase, which additionally incorporates a PWM controller 30 in accordance with an aspect of the present invention. The topology of the present embodiment of the multilevel converter is described in the U.S. Pat. No. 5,625,545, the content of which is incorporated by reference herein for illustrative purposes.

In the example of FIG. 1, the system 1 is a medium voltage drive comprising a three-phase power source providing a power input 2 via lines L1, L2 and L3. The multilevel converter 10 is connected to the AC power input 2 and produces a three-phase AC power supply as output 3, via phase output lines u, v and w. The AC output 3 via lines u, v, and w may be connected to a load 20, which in this example comprises a motor. The motor 20 may be operated by controlling the frequency and/or amplitude of the output voltage produced by the multilevel converter 10.

Each phase of the multilevel converter 10 comprises a respective phase leg 11 formed from a plurality of power cells 12 arranged in a cascaded manner. In the example of FIG. 1, the three phase legs 11 are each formed from the same number of power cells 12, namely three, that are connected in series. Each power cell 12 of a phase is connected to the power input 2 via respective input lines L1, L2 and L3. Power to the input lines L1, L2, L3 may be provided, for example, via a multi-phase winding transformer. The power cells 12 of the three phases are respectively labelled as cell $A_1$ through cell $A_3$, cell $B_1$ through cell $B_3$ and cell $C_1$ through cell $C_3$. Each power cell 12 is responsive to control signals from the PWM controller 30 to alter the voltage level and/or frequency output, resulting in a multilevel voltage waveform for each phase. The power cells 12 generally include power semiconductor switching devices, passive components (inductors, capacitors), control circuits, processors, interfaces, and other components for communicating with the controller 30. The power cells 12 operate based on signals from the controller 30.

Each of the power cells 12 include single-phase inverter circuitry connected to separate DC sources produced by a rectification of the AC power input for each power cell 12 via input lines L1, L2, L3. In this example, the rectification is carried out by diode rectifiers 13a-f arranged in a bridge rectifier configuration. The present example also uses filtering circuitry including, for example, a capacitor 14, for smoothing out voltage ripples from the rectified DC power.

The inverter circuitry of each cell 12 comprises power semiconductor switching devices 15a-d arranged in an H-bridge (also referred to as full bridge) configuration. The switching devices 15a-d may include, for example and without limitation, power transistors such as insulated-gate bipolar transistors (IGBT). The switching devices 15a and 15b connect to cell output line 16a while the switching devices 15c and 15d connect to cell output line 16b. The transistors 15a-d receive pulse width modulation signals, for example, in the form of gate input signals 18, that are controlled by the controller 30 based on pulse width modulation. The controller 30 selects either of transistors 15a or 15b to be ON via a first switching leg 17a, and either of transistors 15c or 15d to be ON via a second switching leg 17b, which will permit power to pass to the load 20 by way of the line 16a or 16b respectively. In other words, a controller 30 triggered switching event of the switching leg 17a causes one of the transistors 15a and 15b to be in an ON state and the other to be in OFF state. Likewise, a controller 30 triggered switching event of the switching leg 17b causes one of the transistors 15c and 15d to be in an ON state and the other to be in OFF state. In the embodiments illustrated, the switching legs 17a and 17b of an individual cell 12 are simply referred to as switching leg A and switching leg B of that particular cell 12.

Each of power cells 12 may be constructed internally to low-voltage standards, despite its inclusion in a medium-voltage apparatus drive 1. By way of example, each power cell 12 may have a 600-volts rating. Thus, the maximum voltage level that can be output by each of power cells 12 is about 600 VDC. Depending on which transistors are ON, the output voltage across the cell output lines 16a and 16b of each power cell may be of either polarity or zero. Thus, each of power cells 12 can have three output states: +600 VDC, −600 VDC, or ZERO VDC. Due to the serial connection between three of the power cells 12 in each phase output line, such as, for example, cell $A_1$, cell $A_2$ and cell $A_3$ to the phase output line u, it is possible to produce a maximum output voltage magnitude of about 1800 VDC for the respective phase output line u. Each power cell 12 may be operated independently of another. Therefore, it is possible to provide at least seven voltage levels per phase to AC motor 20. The approximate values of these line-neutral voltage states include +/−1800 VDC, +/−1200 VDC, +/−600 VDC and ZERO VDC. In general, a cascaded H-bridge multilevel converter having n number of power cells per phase is capable for producing $N_L$ number of line-neutral voltage states for each phase, where $N_L=2n+1$. It should be noted that the line-line voltage may have more levels than the phase (line-neutral) voltage. For example, a cascaded H-bridge multilevel converter may have $2N_L-1$ levels in the line-line voltage. Other topologies may have different number of levels depending on the modulation technique used.

The motor 20 may comprise any type AC-type motor, for example, synchronous, asynchronous, permanent magnet, and may be rated for low voltage, medium voltage or high-voltage. For example, medium-voltage AC motors, such as those used in industrial process control, may operate in the 4.16 kV to 13.8 kV range. Greater or lesser voltage may be used. More than one AC motor 20 may be connected. Other loads may be used instead of or in addition to the motor 20. The AC motor 20 responds to the voltage applied by the multilevel converter on the three phases, for example, to increase, decrease or maintain a speed or position.

The controller 30 may comprise, for example, a processor with a memory, which is capable of storing and executing specific instructions to implement the illustrated PWM control. The controller may be realised, for example and without limitation, by a microcontroller with internal or external memory, or by a fixed-point or floating-point digital signal processor (DSP), or by a programmable logic device (PLD), or any combination of the above mentioned. By pulse-width modulating the voltage reference for each phase, the controller 30 controls each of the power cells 12, and thus, the amplitude and frequency of the voltage output between the output lines 16a and 16b of each power cell 12. A control circuit or control board in a power cell 12 may receive the voltage reference and generate the gating pulses for power switching devices using appropriate vector controls and pulse-width modulation. Alternatively, the controller 30 may output the gating pulses provided to the cells 12 based on the voltage references.

In the proposed modulation method, each phase is assigned a modulating reference signal, for example, having a sinusoidal waveform. For each switching leg A, B of the individual power cells 12, a carrier signal is dynamically allocated. A switching event, i.e. the switching ON or switching OFF of a switching device of the switching leg, is effected by a pulse width modulation signal, for example, as a gate input signal 18, which is triggered by the controller 30 based on a comparison of the carrier signal with the reference signal. However, instead of using a single or fixed triangular or saw-tooth carrier per switching leg as done in the conventional phase-shifted PWM method, the illustrated embodiments use a plurality of carrier signals of different waveform shapes and cycle the carrier signals for each switching leg of each power cell of the multilevel converter. In particular, the proposed method provides that the carrier signal for each switching leg is dynamically selected from a plurality of sets of carrier signals. Each carrier signal of a particular set corresponds to one of a plurality of contiguous bands that fully occupy a range of a waveform of the reference signal. For example, for cascaded H-bridge multilevel converter having a line-neutral phase output voltage with $N_L$ number of levels, there may be $N_L-1$ carrier waveforms in each set. The carriers of a given set have the same amplitude and frequency and different shapes. In this example, the $N_L-1$ carriers of a given set may be arranged into $N_L-1$ contiguous bands that fully occupy the range of the reference signal waveform. Corresponding carriers of different sets are phase-shifted (i.e., delayed by a time interval) from each other, but may be identical in every other respect.

Figure 2A:
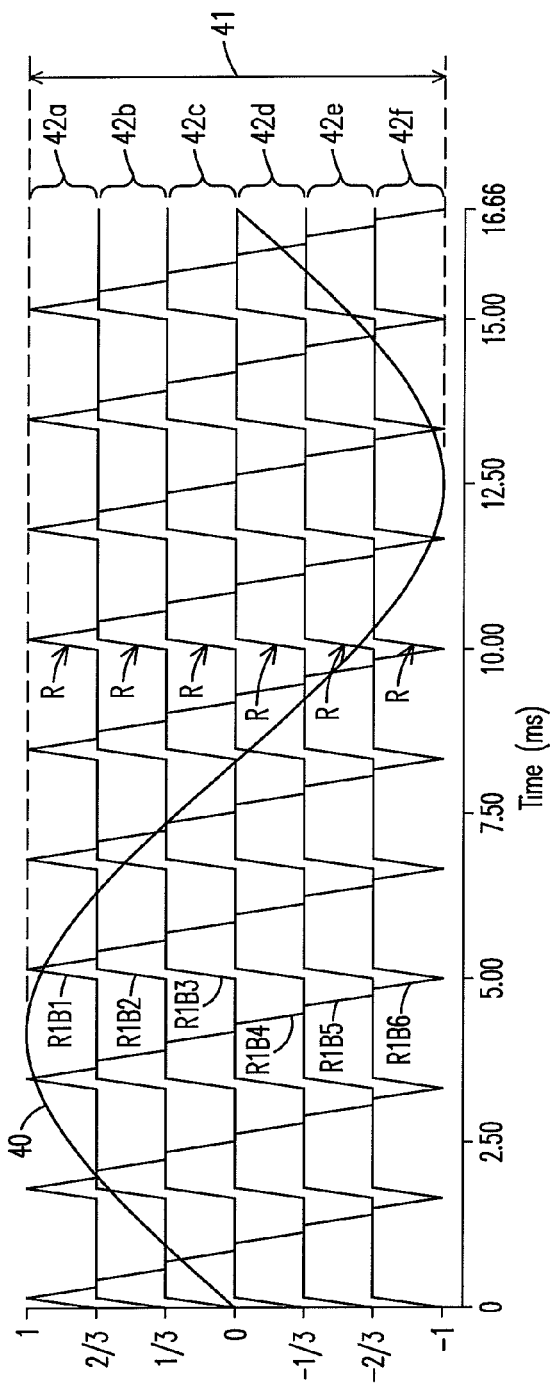
FIG. 2A illustrates a graphical representation of a carrier arrangement with respect to a reference signal waveform for one switching leg, with all rising ramps synchronized.

FIG. 2A illustrates an exemplary carrier set arrangement with respect to the reference signal waveform for one switching leg in the example of FIG. 1. In this example, since there are three cells per phase and each cell can create three levels, there will be a total of seven levels in the phase output voltage (line-neutral). Accordingly, the carriers may be arranged in six contiguous bands equally spaced, in which the range 41 of the reference signal waveform 40 can be divided. The reference signal waveform 40 may also be referred to as a modulating waveform. The range 41 of the reference signal waveform 40 may be referred to as a modulation range of the reference signal. The amplitude of the reference signal waveform 40 is referred to as a modulation index m of the reference signal waveform 40. The illustrated reference signal waveform 40 is a periodic waveform, having, for example, a substantially sinusoidal shape, as depicted in FIG. 2A. It is to be understood that there is no restriction on the shape of the reference signal waveform 40 as long as the waveform 40 is restricted to the interval [−1 1]. The bands 1-6 are respectively labelled as 42a-f, while the carriers are labelled R1B1, R1B2, R1B3, R1B4, R1B5 and R1B6.

Figure 2B:
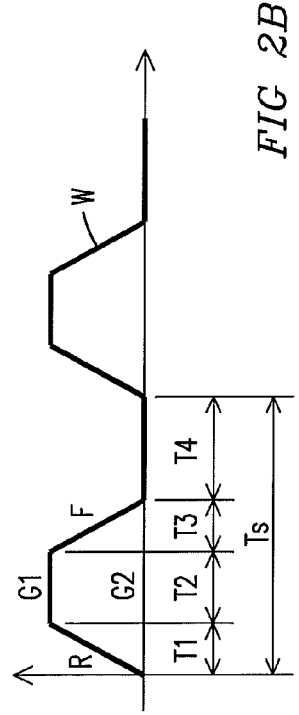
FIG. 2B illustrates a graphical representation of a generalized shape of a trapezoidal carrier waveform in accordance with an exemplary embodiment of the present invention.

In the illustrated example each of the carriers has a waveform shape which may be described in general terms referring to FIG. 2B. Each carrier has a periodic waveform W, such that the waveforms W of all the carrier have the same switching period Ts. In FIG. 2B, two consecutive switching periods of the waveform W are shown. Each carrier waveform W comprises a first portion R, which corresponds to a rising ramp of the carrier signal and a second portion F, which corresponds to falling ramp of the carrier signal. Additionally, each carrier waveform W also comprises at least one flat portion G1 or G2, wherein the carrier signal is substantially constant. The portion G1 represents a maximum or peak value of the carrier signal whereas the portion G2 represents a minimum value of the carrier signal. The portions R, G1, F and G2 correspond to period T1, T2, T3 and T4 respectively. The periods T1 and T3 are identical in all the carriers in FIG. 2A, where the difference from one carrier to another is the length of T2 and T4. The periods in this example are thus related as:

$$Ts = T1+T2+T3+T4 = 2T1+T2+T4 \qquad (1)$$

In the illustrated embodiment, for each carrier, at least one of the periods T2 and T4 is non-zero. That is, for a given carrier, the periods T2 and T4 may be both non-zero (as depicted in FIG. 2B) or may be individually zero, but are not both zero at the same time. Thus, the waveform W, as described in general terms, would comprise a rising ramp R, a falling ramp F, and at least one flat portion G1 and/or G2. Such a waveform is referred to herein as a trapezoidal waveform. The illustrated trapezoidal waveform is in contrast to a triangular or a saw-tooth waveform as used in the conventional PS-PWM method where both T2 and T4 are zero for each carrier, i.e., their waveforms do not have any flat portion.

In the example of FIG. 2A, the carrier of band 1 (labelled 42a) has T2=0, while the carrier for band 6 (labelled 42f) has T4=0. Each of the illustrated carriers has a trapezoidal waveform shape, having the same amplitude and frequency, while having different shapes. In particular, flat portions defined by the periods T2 and T4 vary from bands 1 through 6. The six bands 1 through 6 fully occupy the range 41 of the reference signal waveform 40. Each band covers ⅙ of the range 41 of the reference signal waveform 40. In other words, the bands 42a-f may be defined as flows:

Band 1: ⅔<reference signal waveform<1
Band 2: ⅓<reference signal waveform<⅔
Band 3: 0<reference signal waveform<⅓
Band 4: -⅓<reference signal waveform<0
Band 5: -⅔<reference signal waveform<-⅓
Band 6: -1<reference signal waveform<-⅔

In contrast to the phase-shifted PWM principle, in the presently described method, the carrier waveform changes its shape depending on where the reference signal lies with respect to the bands identified above. As an example, FIG. 2A shows the carrier disposition for one switching leg of one cell, in this case leg A of cell $A_1$. Thus, in this example, for the switching leg A of cell $A_1$ the set of carriers referred to as R1B1, R1B2, R1B3, R1B4, R1B5 and R1B6 respectively correspond to the bands 1 through 6. In one embodiment, switching leg B of cell $A_1$ may have its set of six carriers displaced by a predefined time interval Td with respect to the references shown in FIG. 2A. The set of carriers for switching leg B of cell $A_1$ are referred to herein as R2B1, R2B2, R2B3, R2B4, R2B5 and R2B6, that respectively correspond to the bands 1 through 6. Each switching leg of the other two cells $A_2$ and $A_3$ may have the respective carriers displaced by additional Td. For example, switching leg A of cell $A_2$ may have a displacement Td with respect to switching leg B of cell $A_1$ and 2 Td with respect to switching leg A of the same cell, $A_1$. The last switching leg of the last cell of the phase has a set of carriers referred to as R6B1, R6B2, R6B3, R6B4, R6B5 and R6B6, which respectively correspond to the bands 1 through 6.

In the illustrated embodiment, the time interval Td is chosen such that Td=Ts/2n, where Ts is a switching period defined as $T_s = 1/f_{switching}$, $f_{switching}$ being the switching frequency, and n is the number of power cells per phase. In the illustrated embodiment, the interval Td is also related to the periods T1 and T3 (see FIG. 2B) as follows:

$$T1 = T3 = Td/2 \qquad (2)$$

Each switching leg is allocated one of the six carriers once the band is identified. For example if the reference signal waveform is between ⅔ and 1, then it is determined that band 1 is active and as such the top carrier in FIG. 2A will be used by the switching leg A (left pole) of cell $A_1$. If the reference signal waveform is between -⅔ and -1, then it is determined that band 6 is active and as such the bottom carrier in FIG. 2A will be used by the switching leg A of cell $A_1$. Each of the six bands thus has a correspondent in one of the six carriers in FIG. 2A. With respect to FIG. 2A, where the left pole carriers are displayed, the carriers for switching leg B (right pole) are shifted by Td. Similarly, all other poles of the remaining cells of one phase are further shifted by Td. It follows that a total 36 carriers are needed for this implementation. For a general case where n cells are used on each phase, the total number of carriers equals $(2n)^2$.

It is to be noted that in order to have the same number of switching events as compared to a phase-shifted PWM implementation, the following relationship applies:

$$Td = \frac{T_{PWM\_PHASE-SHIFTED}}{2 \cdot N} \qquad (3)$$

where $T_{PWM\_PHASE-SHIFTED}$ is the period of the triangular carrier used in a phase-shifted implementation of the modulator and Td is the time displacement between the carriers associated to switching legs A and B of the same cell.

Figure 3:
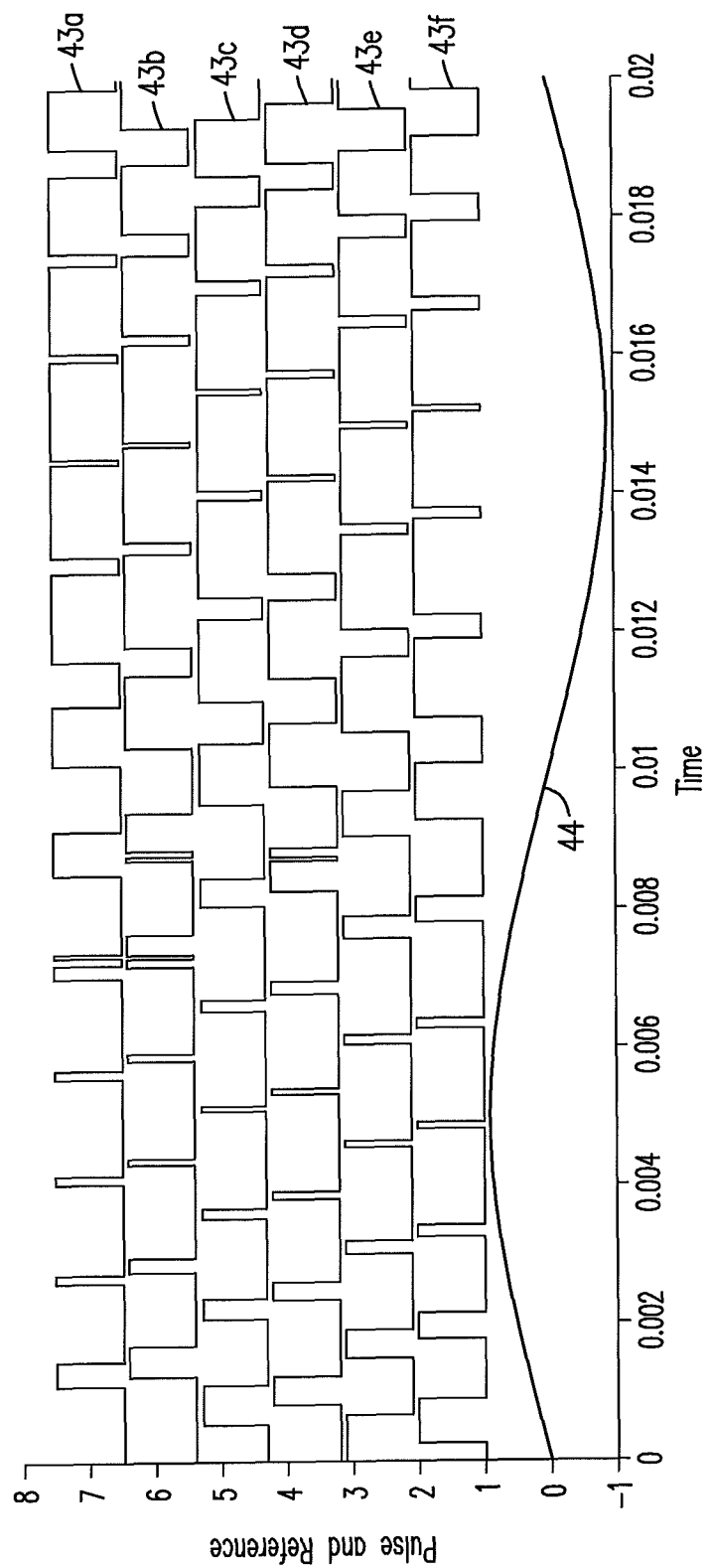
FIG. 3 illustrates a graphical representation of pulses and reference signal waveform for modulation index m=0.9, for the carrier arrangement of FIG. 2A, in accordance with an exemplary embodiment of the present invention.
Figure 4:
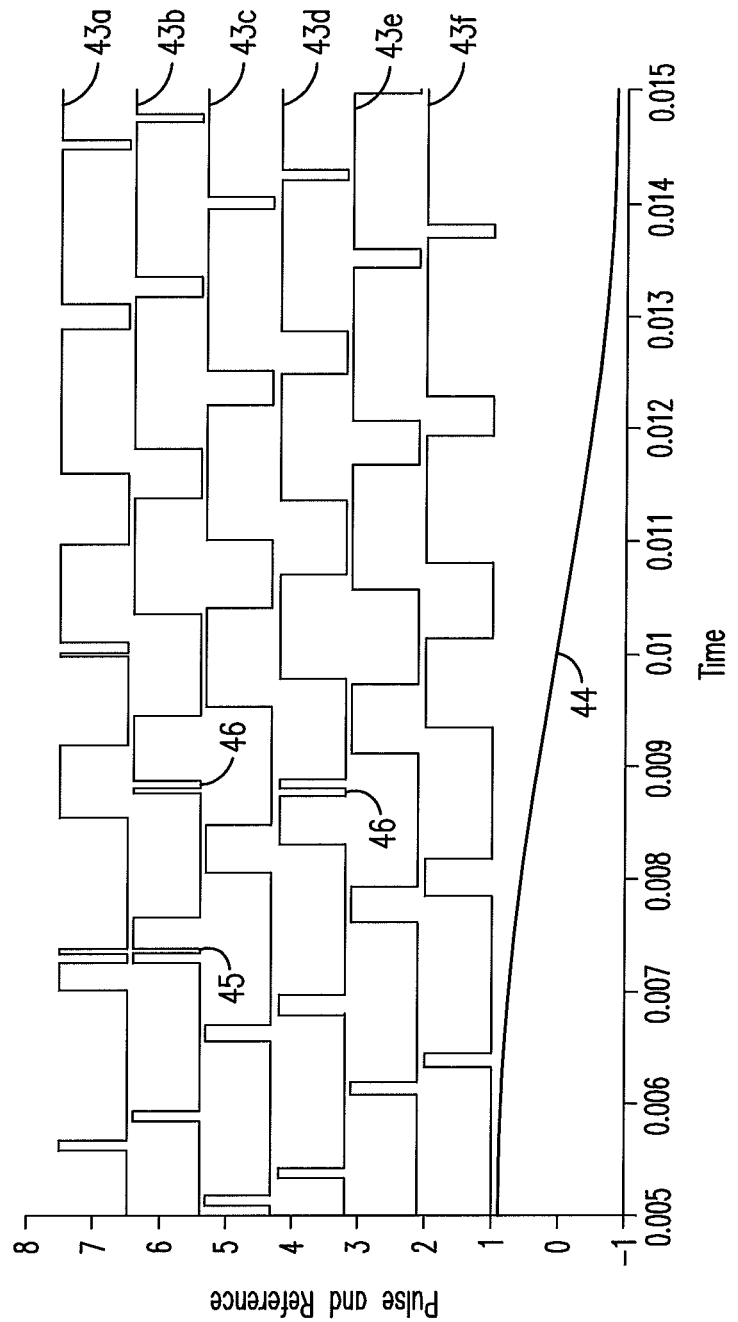
FIG. 4 shows a graphical representation of distortion of the pulses and reference due to bands crossover for the pulses shown in FIG. 3.

In the example illustrated above, an individual switching leg is dynamically allocated a carrier that corresponds to the band instantaneously occupied by the reference signal. However, a change in shape of the carrier waveform during a transition between bands would give rise to pulse distortions, i.e. increased number of switching events, at the transitions between the bands. This would be reflected in additional pulses, i.e. additional switching events leading to uneven distribution of pulses between the cells. This effect is particularly evident in cases where the switching frequency is low, which is generally the case in all practical applications as the cascaded H-bridge topology is primarily used in medium/high voltage application where the switching frequency is restricted to a few hundred hertz to 1 kHz. This phenomenon is illustrated in FIGS. 3 and 4 which depict the transistor pulses 43a-f in one switching leg of each cell for one phase for a reference signal waveform 44 having modulation index m=0.9. It is discernable that some of the transistor pulses 43a-f are negatively affected when the bands are crossed, i.e., during a transition from a first band to a second band.

FIG. 4 is a zoomed-in view of FIG. 3, showing in detail the distortion of the pulses 43a-f due to bands crossover. For example, in FIG. 4, pulse distortions at the transition from band 1 to band 2 are indicated by the reference numeral 45, while pulse distortions at the transition from band 2 to band 3 are indicated by the reference numeral 46.

It is to be noted that the carriers in FIG. 2A are arranged in the bands 1 through 6 such that they have synchronized rising ramps R, which is to say that the rising ramps R of the carriers start and end at substantially the same time instants. One of the findings in which embodiments of the present invention are based on is that if the carriers, from the plurality of sets of carriers mentioned above, are instead arranged in the bands 1 through 6 such that they have synchronized falling ramps, the distortion seen in FIGS. 3 and 4 are not present.

Figure 5:
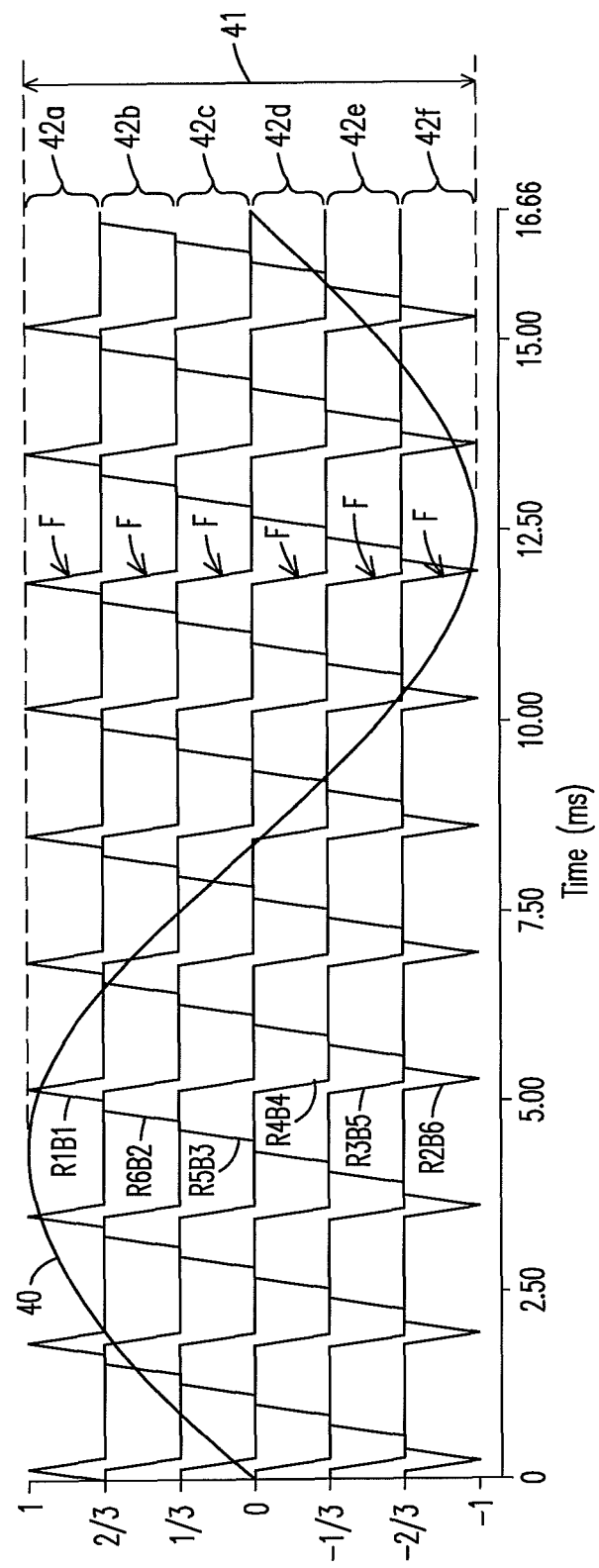
FIG. 5 illustrates a graphical representation of a carrier arrangement with respect to a reference signal waveform for one switching leg, with all falling ramps synchronized, in accordance with an exemplary embodiment of the present invention.

FIG. 5 shows a carrier arrangement with the reference signal waveform 40 wherein all the carriers have their falling ramps F synchronized, which is to say that the falling ramps F of the carriers start and end at substantially the same time instants. With respect to the grouping of carriers defined in the present example, the carriers represented in FIG. 4 would be the carriers R1B1, R6B2, R5B3, R4B4, R3B5 and R2B6 arranged respectively in the bands 1 through 6. It is seen that in this example of carrier disposition with synchronized falling ramps, when the reference signal waveform 40 has negative slope, the transition from one band to the next one down does not lead to distortions in the transistors pulses, whereas when the reference signal waveform 40 has a positive slope, there will be distortions at the transition from one band to the next one up.

Embodiments of the present invention are based on an inventive recognition that: when the slope of the reference signal waveform 40 is positive (i.e., reference signal is increasing), in order to avoid pulse disruptions, the rising ramps of the carrier from both outgoing and ingoing bands must be synchronized, which is the case in FIG. 2A. Similarly, when the slope of the reference signal 40 is negative (i.e., reference signal is decreasing), in order to avoid pulse disruptions, the falling ramps of the carrier from both outgoing and ingoing bands must be synchronized, which is the case in FIG. 5.

Embodiments of the present invention are implemented by making available, for each switching leg, the entirety of the multiple sets of carriers to select from. For a cascaded H-bridge multilevel converter with n power cells connected in series per phase, there would be a total of $(2n)^2$ carriers which may be divided into 2n sets of carriers. In the illustrated example, there are a total of 36 carriers, divided into six sets comprising six carriers each. Therefore there is a large degree of freedom on how to distribute these carriers to a specific switching leg. Instead of using the same set of carriers for a certain switching leg irrespective of where the reference signal waveform lies with respect to the bands defined above, embodiments of the invention dynamically select the carriers for a certain switching leg from across multiple sets of carriers (as opposed to a fixed set of carriers) to follow the following rule, namely: when there is a transition of the reference signal from a first band to a second band where the second band is higher than the first band, then the rising ramps of the carriers for both first band and the second band are synchronized; and when there is transition from first band to a second band where the second band is lower than the first band, then the falling ramps of the carriers for both the first and second bands are synchronized. The second band is said to be higher than the first band if the slope of the reference signal waveform is positive at the transition from the first band to the second band. The second band is said to be lower than the first band if the slope of the reference signal waveform is negative at the transition from the first band to the second band. Using the above rule for the illustrated PWM control method, it becomes possible to rotate all available carriers and assign the proper carrier to a given switching leg in a manner that will not disrupt the PWM pulse when a band is crossed. In this way the PWM pulses are directly generated for each switching leg once the correct carrier is assigned.

Figure 6:
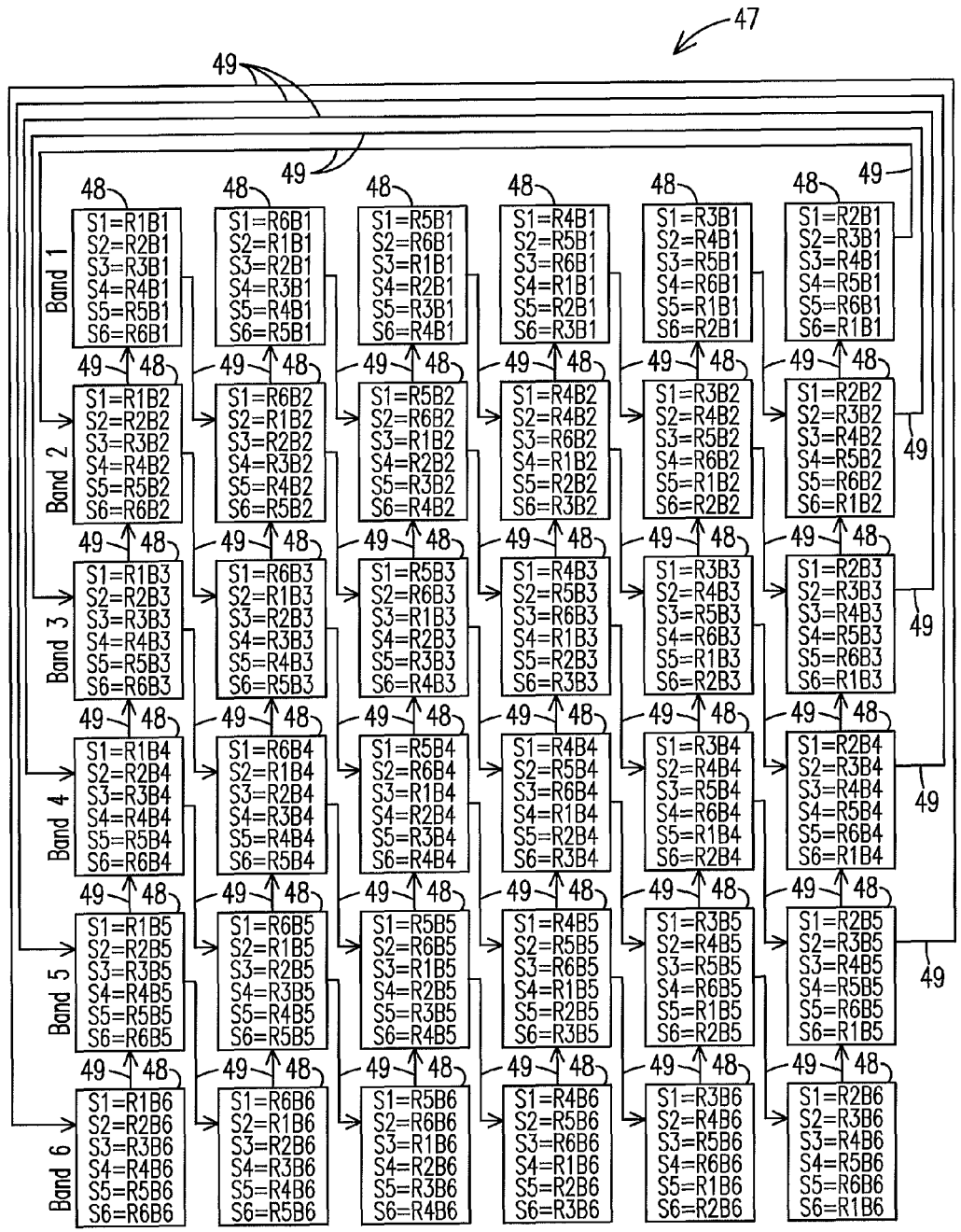
FIG. 6 illustrates a schematic of an example of a finite state machine which dynamically allocates the carriers for all the switches of each switching leg for a cascaded H-bridge multilevel converter having a three cells/phase topology, in accordance with an exemplary embodiment of the present invention.

In one embodiment, the dynamic allocation of the carriers is carried out by using a finite state machine to distribute the carriers to the switching legs associated with each phase on a cyclical basis. FIG. 6 illustrates an example of finite state machine 47 which dynamically allocates the carriers for all the switches of one leg, based on the exemplary carrier grouping in the illustrated embodiment. Every horizontal row contains the carrier allocations inside a particular band, Bx where x=1 . . . 2n, where n is the number of power cells per phase. In this particular case there are three cells per each phase, therefore there are six bands. In FIG. 1, switching devices of the cell $A_3$, cell $A_2$ and cell $A_1$ are labelled as $A_3\_A\_Top$, $A_3\_B\_Top$, $A_3\_A\_Bot$, $A_3\_B\_Bot$, $A_2\_A\_Top$, $A_2\_B\_Top$, $A_2\_A\_Bot$, $A_2\_B\_Bot$, $A_1\_A\_Top$, $A_1\_B\_Top$, $A_1\_A\_Bot$ and $A_1\_B\_Bot$. Referring back to FIG. 6, the labels S1, S2, S3, S4, S5 and S6 refer to the carriers used by switching devices $A_3\_A\_Top$, $A_3\_B\_Bot$, $A_2\_A\_Top$, $A_2\_B\_Bot$, $A_1\_A\_Top$, $A_1\_B\_Bot$, respectively. The carriers RxBy were defined previously, where R1By (y=1 . . . 6) are displayed in FIG. 2A. The carriers R2By (y=1 . . . 6) are simply the carriers R1By delayed by the time interval Td, the carriers R3By (y=1 . . . 6) are the carriers R1By delayed by a time interval 2 Td and so far. Finally, the carriers R6By (y=1 . . . 6) are obtained from the carriers R1By by a delay of 5 Td. The interval Td is selected such that Td=Ts/2n, where Ts denotes a switching period defined as Ts=1/$f_{switching}$, $f_{switching}$ being the switching frequency, and n is the number of power cells per phase of the cascaded H-bridge multilevel converter. In FIG. 6, the blocks 48 illustrate the carrier allocations to the six switching devices for a band instantaneously occupied by the reference signal, while the arrows 49 represent transitions or crossovers of the reference signal from one band to another.

Figure 7:
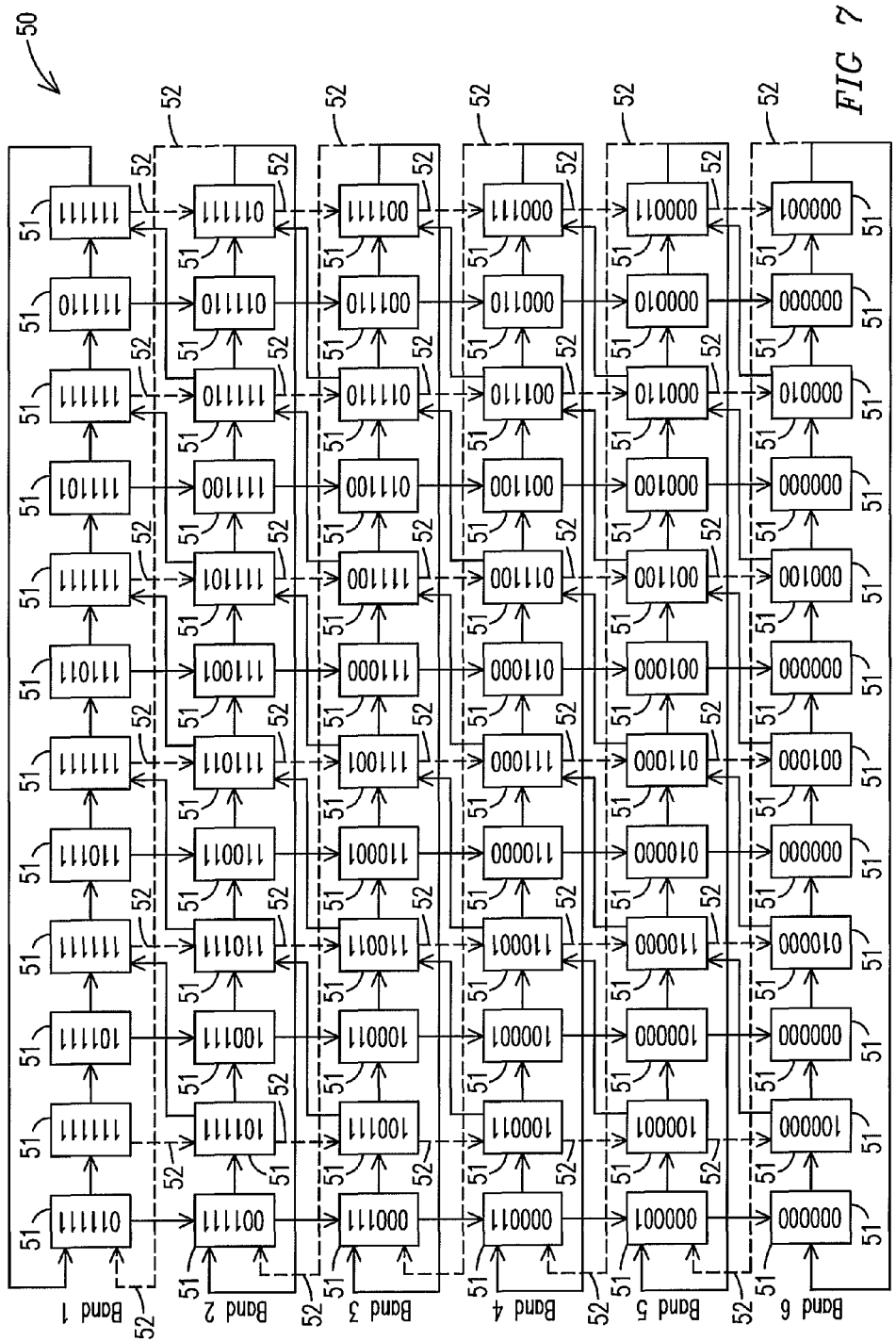
FIG. 7 illustrates a schematic of state transitions based on a proposed carrier allocation method for a cascaded H-bridge multilevel converter having a three cells/phase topology, in accordance with an exemplary embodiment of the present invention.

Assuming that each of the six devices of the above example is assigned a value of 0 if they are OFF and a value of 1 if they are ON, a state diagram can be drawn showing all the possible states per phase generated by using the carrier allocation method in FIG. 6. FIG. 7 illustrates an exemplary state diagram 50, where the 2n digits binary number (6 digits in this case, since n=3, where n is the number of power cells per phase) directly indicates if the switching devices $A_3\_A\_Top$, $A_3\_B\_Bot$, $A_2\_A\_Top$, $A_2\_B\_Bot$, $A_1\_A\_Top$, $A_1\_B\_Bot$ are ON or OFF. The diagram shown in FIG. 7 confirms that at every state 51 only one device switches per phase and that there are no pulse disruptions at the band crossings. It is to be noted that the dashed lines 52 in FIG. 7 indicate transitions to or from the same states into a different band and they could be ignored. They are shown here just for the ease of understanding how a transition from one band to another band using the illustrated method keeps the same state and therefore does not introduce any disruption in the pulse generation. For example, from state 111111 in band 1 it is possible to move to the same state 110111 which may be located in band 1, if there is no band transition or, in band 2 if there is a band transition.

The finite state machine may be implemented by the controller 30 by providing suitable instructions/algorithms to the controller 30. It will be understood that in addition to or alternate to a finite state machine, any other technique or algorithm may be implemented that is capable of picking the appropriate carrier based on the allocation rule specified above.

A discernable result provided by the illustrated embodiments is that it is ensured that on each phase, only one switching leg switches at every switching instance, including when a transition occurs from one band to another one. The embodiments also ensure that each switching leg exhibits the same number of switching events, unaffected by the transition from a band to another one. This is illustrated in FIG. 8-9.

Figure 8:
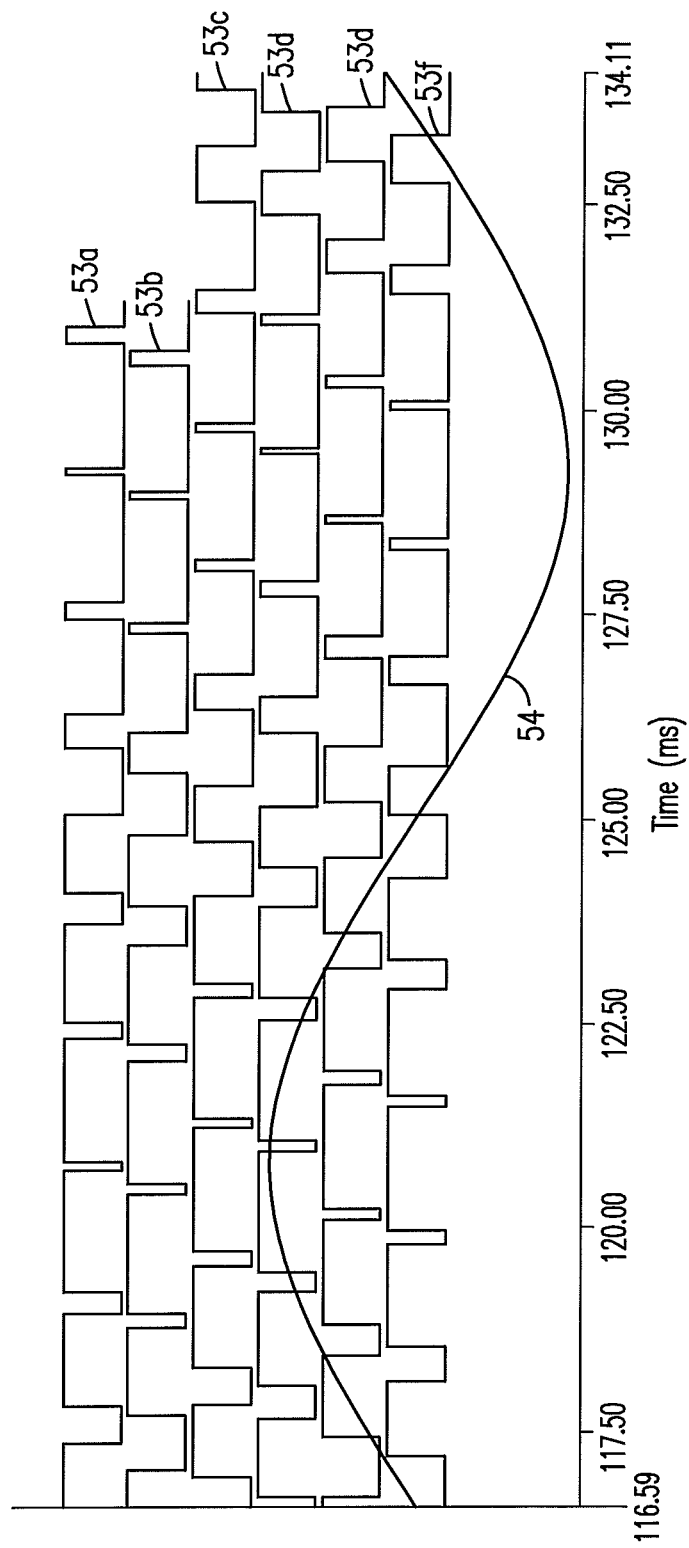
FIG. 8 shows a graphical representation of pulses obtained using a proposed carrier allocation method for a continuous reference, in accordance with an exemplary embodiment of the present invention.
Figure 9:
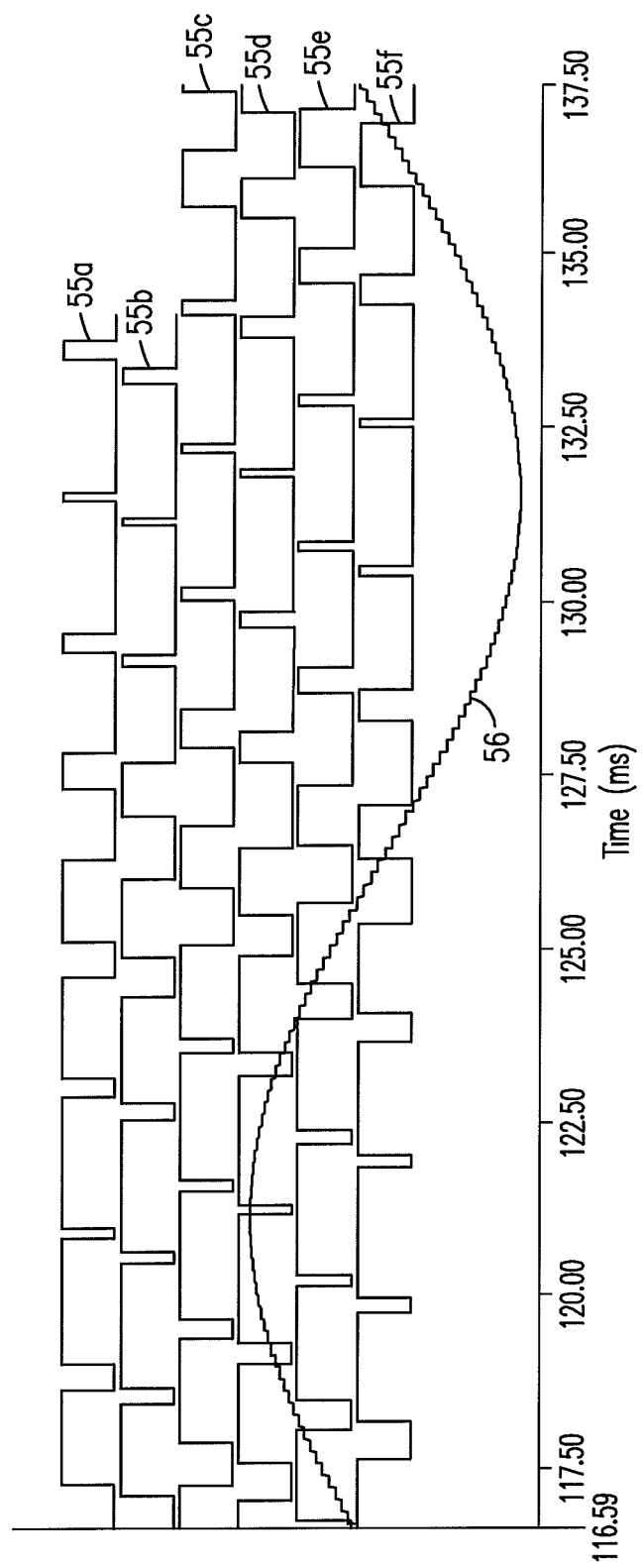
FIG. 9 shows a graphical representation of pulses obtained using a proposed carrier allocation method for a sampled reference, in accordance with an exemplary embodiment of the present invention.

FIG. 8 illustrates the six pulses for $A_3\_A\_Top$, $A_3\_B\_Bot$, $A_2\_A\_Top$, $A_2\_B\_Bot$, $A_1\_A\_Top$, $A_1\_B\_Bot$, labelled 53a-f respectively, using the illustrated carrier allocation method for a continuous sinusoidal reference signal 54. FIG. 9 illustrates the six pulses for $A_3\_A\_Top$, $A_3\_B\_Bot$, $A_2\_A\_Top$, $A_2\_B\_Bot$, $A_1\_A\_Top$, $A_1\_B\_Bot$, labelled 55a-f respectively, using a sampled sinusoidal reference signal 56. A discernable difference with respect to FIG. 3-4, is that in FIG. 8-9 there are no pulse disruptions, i.e., additional switching events, during any of the bands transitions, wherein the pulses are uniformly distributed to all switching devices per phase.

Simulation Results

FIG. 10 through FIG. 13 illustrate simulation results that demonstrate differences in the quality of output voltages and currents obtained by the above described modulation method in comparison to the conventional method of phase-shifted PWM (PS-PWM) for a cascaded H-bridge multilevel converter with three cells per phase. In this case, the PS-PWM uses 18 saw-tooth carriers wherein each switching leg is assigned a fixed carrier while the illustrated method uses 36 carriers that are dynamically allocated to the individual switching legs.

Figure 10:
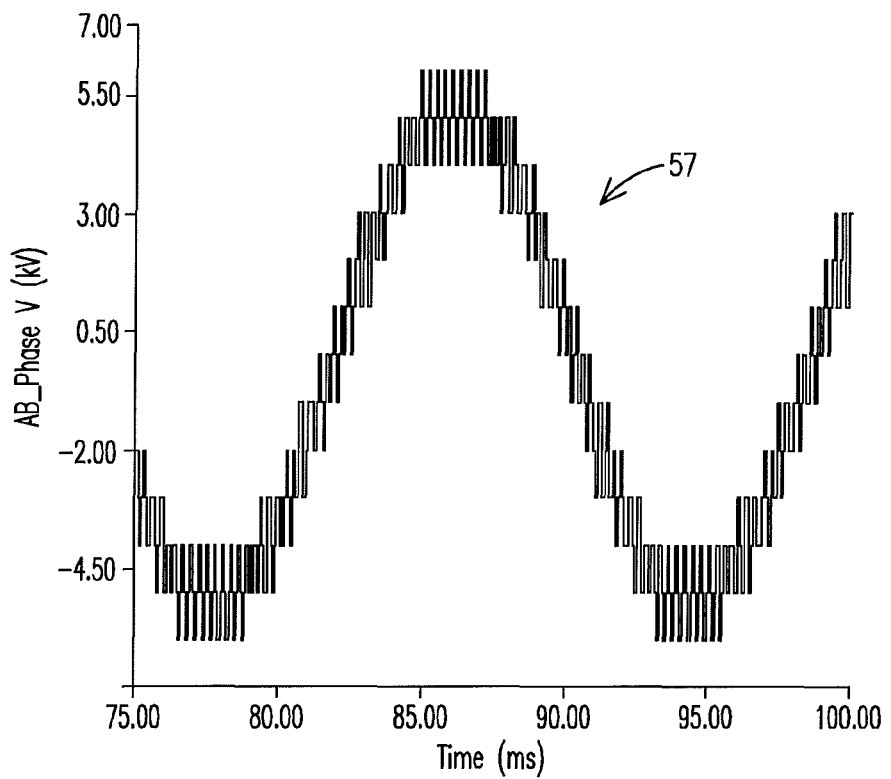
FIG. 10 illustrates a graphical representation of a simulated line-line voltage spectrum obtained with PS-PWM in a cascaded H-bridge multilevel converter for m=1, $f_{out}$=60 Hz, $f_{switching}$=600 Hz.
Figure 11:
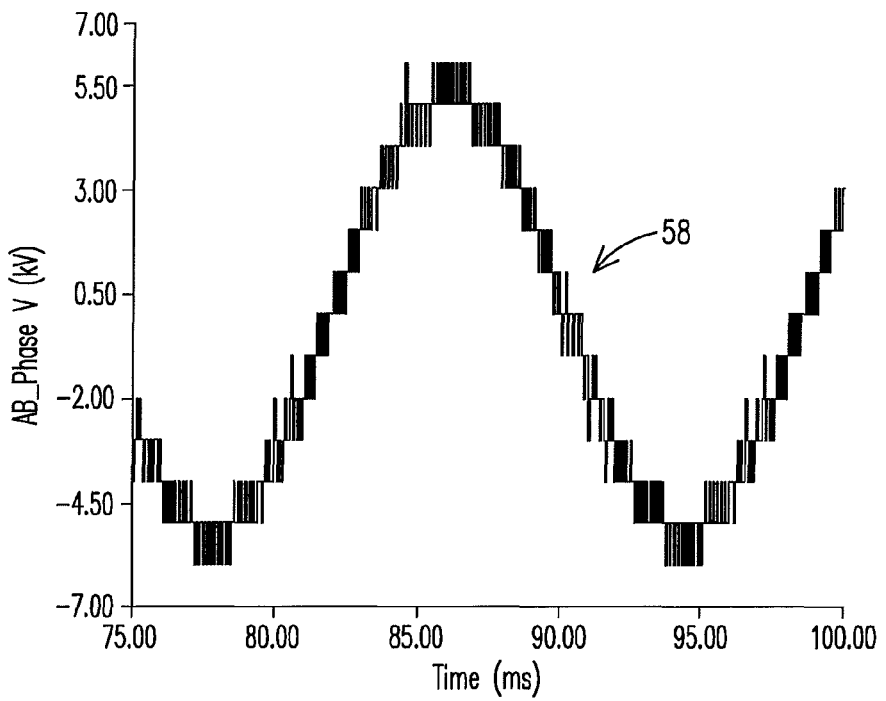
FIG. 11 illustrates a graphical representation of a simulated line-line voltage spectrum obtained with an illustrated modulation method in a cascaded H-bridge multilevel converter for m=1, $f_{out}$=60 Hz, $f_{switching}$=600 Hz.

FIG. 10 illustrates a simulated line-line voltage spectrum 57 obtained with PS-PWM in a cascaded H-bridge multilevel converter for modulation index m=1, output frequency $f_{out}$=60 Hz, and switching frequency $f_{switching}$=600 Hz. As clear from FIG. 10, from a given voltage level, there are transitions both toward the next level up and the next level down, thus introducing additional harmonics. FIG. 11 illustrates a simulated line-line voltage spectrum 58 obtained with the illustrated modulation method in a cascaded H-bridge multilevel converter for m=1, $f_{out}$=60 Hz, $f_{switching}$=600 Hz. As discernable, the illustrated method provides that if the slope of the reference signal waveform is positive, transitions mostly take place from a given level to the next level up, whereas if the slope of the reference signal waveform is negative, transitions mostly take place from a given level to the next level down.

Figure 12:
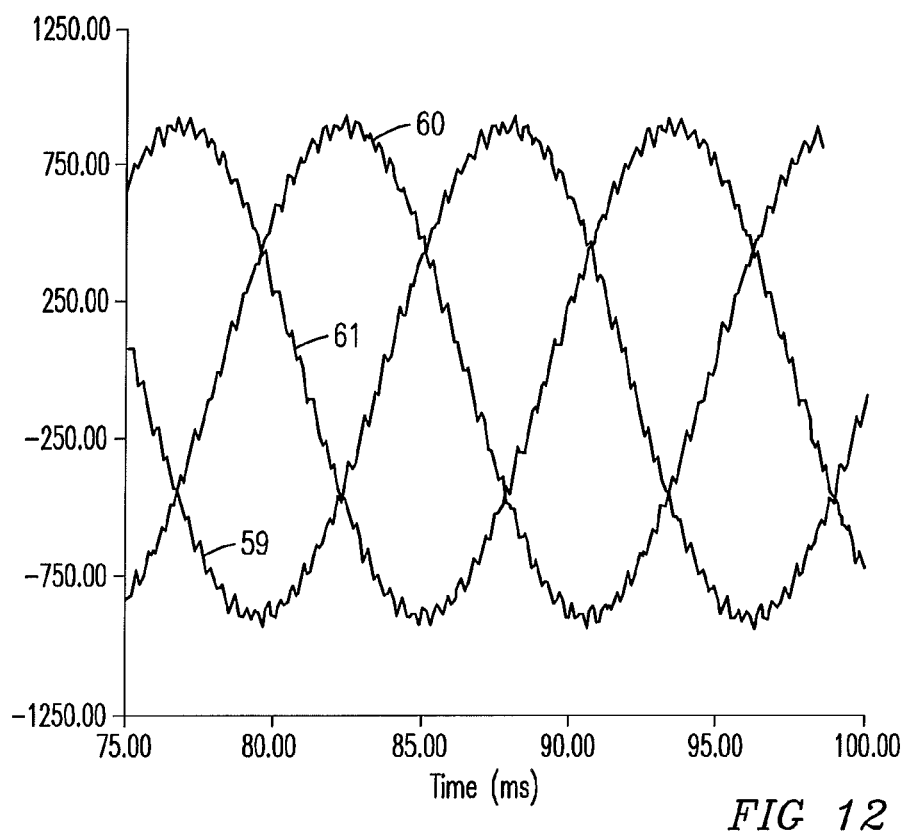
FIG. 12 illustrates a graphical representation of simulated output currents obtained with PS-PWM in a cascaded H-bridge multilevel converter for m=1, $f_{out}$=60 Hz, $f_{switching}$=420 Hz.
Figure 13:
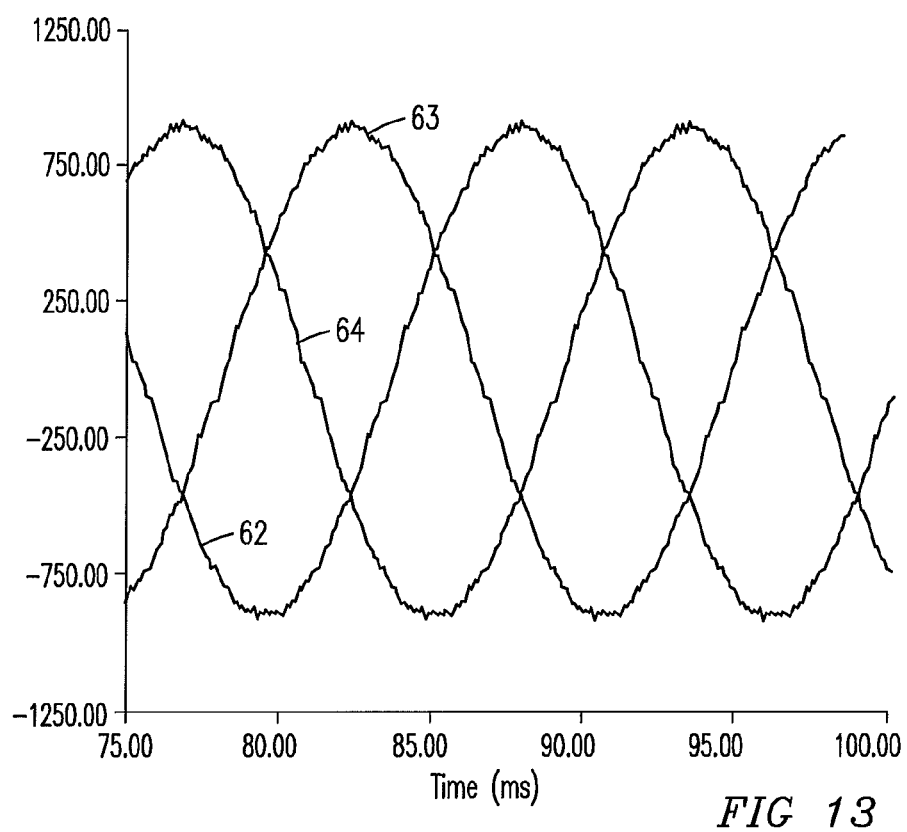
FIG. 13 illustrates a graphical representation of simulated output currents obtained with an illustrated modulation method in a cascaded H-bridge multilevel converter for m=1, $f_{out}$=60 Hz, $f_{switching}$=420 Hz.

FIG. 12 illustrates simulated phase currents 59, 60, 61 obtained with PS-PWM in the cascaded H-bridge multilevel converter for m=1, $f_{out}$=60 Hz, $f_{switching}$=420 Hz. FIG. 13 illustrates simulated phase currents 62, 63, 64 obtained with the illustrated modulation method in a cascaded H-bridge multilevel converter for m=1, $f_{out}$=60 Hz, $f_{switching}$=420 Hz.

Example 2

Modular Multilevel Converter ($M^2C$)

Modular multilevel converters also referred to as $M^2C$, can be used, for example, as voltage source converters for producing high-voltage direct current (HVC).

Figure 14:
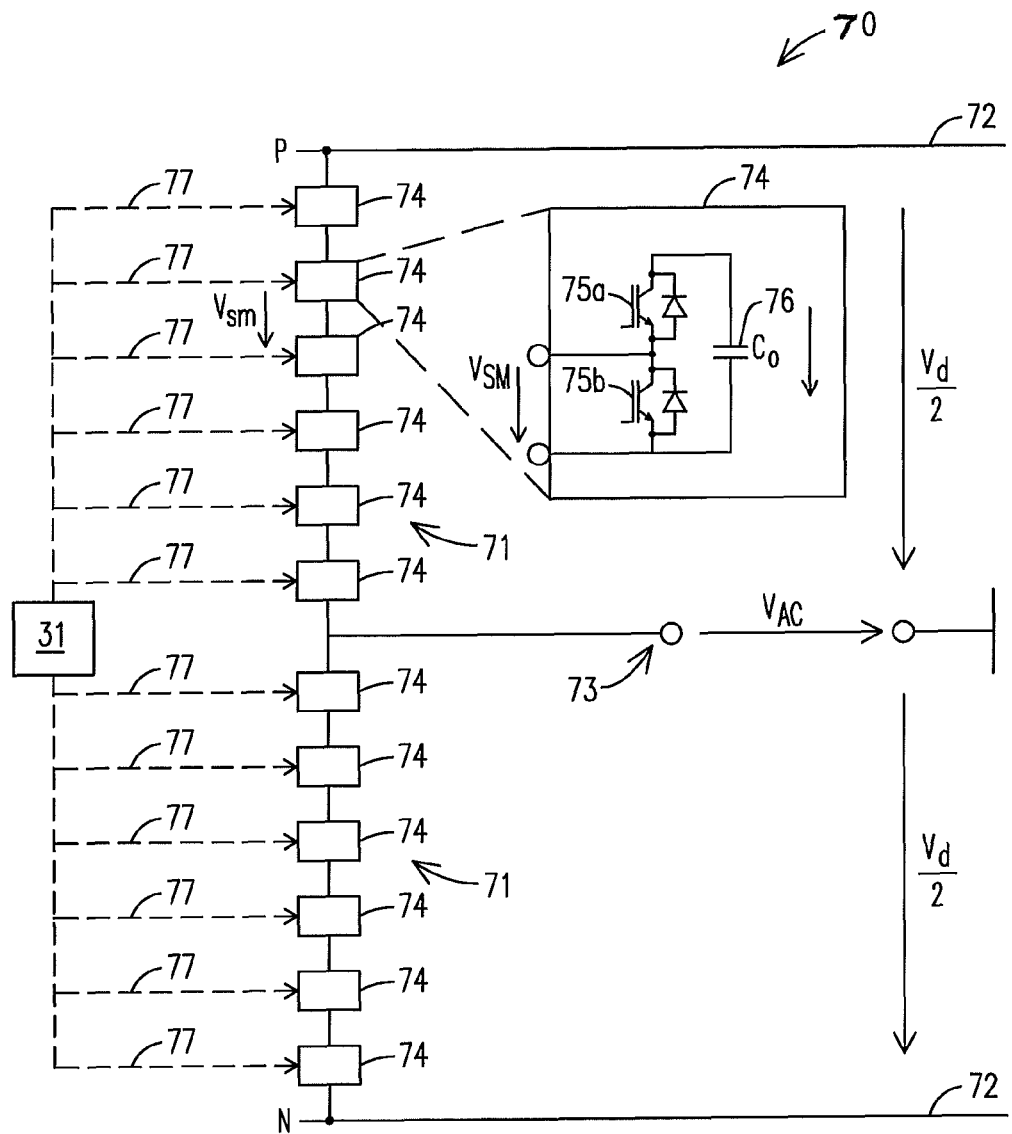
FIG. 14 is a schematic diagram illustrating a modular multilevel converter leg having a six sub-modules/arm topology in accordance with a second example embodiment.

FIG. 14 illustrates a modular multilevel converter 70 that includes a PWM controller 31 in accordance with a second embodiment of the present invention. The topology of an $M^2C$ is generally known and will not be described in great detail herein. Briefly, the $M^2C$ 70 illustrated in FIG. 14 includes two arms 71 per phase. Although only one phase is illustrated in FIG. 14, the $M^2C$ 70 may include multiple phases, for example three phases. Each arm 71 connects a DC input terminal 72, to an AC output terminal 73. A DC voltage Vd is applied across the DC input terminal 72. Each arm 71 is effectively a high-voltage controlled switch comprising a plurality number of independently operable power cells 74 connected in series. Each power cell 74 of an M2C is referred to as a sub-module. In the illustrated embodiment, there are six sub-modules per arm 71.

Each power cell or sub-module 74 of the exemplary $M_2C$ 70 includes a half-bridge inverter circuit comprising switching devices 75a and 75b connected in series across a capacitor 76 with the midpoint connection and one of the two capacitor terminals brought out as an external connection. The switching devices 75a and 75b include, for example, power transistors, such as IGBTs or any other type of semiconductor switches. Each sub-module 74 may be operated as a two-level converter (i.e., with two output voltage states namely $V_{SM}$ and ZERO), by appropriately controlling the switching devices 75a and 75b via pulse width modulation signals, such as gate input signals 77 generated by the PWM controller 31. In this example, since each sub-module 74 has a half-bridge inverter configuration, switching of the switching devices 75a and 75b are implemented in one switching leg. Herein, a controller 31 triggered switching event of the switching leg causes one of the switching devices 75a and 75b to be in an ON state and the other to be in OFF state.

Although not shown, the current via line outputs 73 may be fed to a load, such as a motor. The three-phase $M^2C$ topology illustrated herein does not provide a specific phase voltage as does the cascaded H-bridge topology. The $M^2C$ provides line-line voltages, which is generally sufficient, especially for motor applications where it is the line-line voltage that is of relevance as the neutral is inside the motor.

By pulse-width modulating the voltage reference for each phase, the controller 31 controls each of the sub-module 74. A control circuit or control board in a sub-module 74 may receive the voltage reference and generate the gating pulses for power switching devices 75a and 75b using appropriate vector controls and pulse-width modulation. Alternatively, the controller 31 may output the gating pulses provided to the sub-modules 74 based on the voltage references.

In the proposed modulation method, each phase is assigned a modulating reference signal, for example but not necessarily, having a substantially sinusoidal waveform. From each phase reference signal, arm reference signals are developed for each of the two arms 71 of the particular phase. In this case, each sub-module has a single switching leg for which a carrier is dynamically allocated from a plurality of sets of carriers of different shapes. For the switching leg of each sub-module 74, a switching event, i.e. the switching ON or switching OFF of a switching device of the switching leg, is effected by the gate input signal 77, which is triggered by the controller 31 based on a comparison of the carrier signal with the arm reference signal. As in the earlier embodiment, the present embodiment use a plurality of carrier signals of different waveform shapes and cycle the carrier signals for each switching leg. The method provides that the carrier signal for each switching leg is dynamically selected from a plurality of sets of carrier signals. The number of sets of carrier signals for each arm 71 in this example equals n, where n is the number of sub-modules 74 per arm 71 of the phase. Each carrier signal of a particular set corresponds to one of a plurality of contiguous bands that fully occupy a range of a waveform of the arm reference signal. The carriers of a given set have the same amplitude and frequency and different shapes. In this example, the six (in general, n) carriers of a given set may be arranged into six (in general, n) contiguous bands that fully occupy the range of the arm reference signal waveform. Corresponding carriers of different sets are phase-shifted (i.e., delayed by a time interval) from each other, but may be identical in every other respect. The dynamically selected carrier signal corresponds to a band that is instantaneously occupied by the arm reference signal.

As per the present method, for a modular multilevel converter topology having n sub-modules or power cells per arm, the total number of carriers generated for each phase is $n^2$. The carrier for each switching leg can thereby be selected from the entirety of $n^2$ trapezoidal waveforms such that the following allocation rule is met, namely: when there is a transition of the arm reference signal from a first band to a second band where the second band is higher than the first band, then the rising ramps of the carriers for both first band and the second band are synchronized; and when there is transition from first band to a second band where the second band is lower than the first band, then the falling ramps of the carriers for both the first and second bands are synchronized. The second band is said to be higher than the first band if the slope of the arm reference signal waveform is positive at the transition from the first band to the second band. The second band is said to be lower than the first band if the slope of the arm reference signal waveform is negative at the transition from the first band to the second band. Using the above rule for the illustrated PWM control method, it becomes possible to rotate all available carriers and assign the proper carrier to a given switching leg in a manner that will not disrupt the PWM pulse when a band is crossed. In this way the PWM pulses are directly generated for each switching leg once the correct carrier is assigned.

In the illustrated embodiment, for the above-mentioned modular multilevel converter topology, the carriers allocated to the switching legs of adjacently connected power cells 74 are displaced in time by an interval Td, where Td=Ts/n, where Ts is a switching period defined as Ts=1/$f_{switching}$, $f_{switching}$ being the switching frequency, and n is the number of power cells per arm.

In one embodiment, the dynamic allocation of the carriers is carried out by using a finite state machine to distribute the carriers to the switching legs associated with each phase on a cyclical basis as explained above with respect to the cascaded H-bridge multilevel converter. In this case, the carriers are distributed to each switching leg from a total of 36 carriers, divided into six sets of carriers, with six carriers in a set that are arranged in six contiguous bands that fully occupy the arm reference signal waveform. The finite state machine may be implemented by the controller 31 by providing suitable instructions/algorithms to the controller 31. It will be understood that in addition to or alternate to a finite state machine, any other technique or algorithm may be implemented that is capable of picking the appropriate carrier based on the allocation rule specified above.

Figure 15:
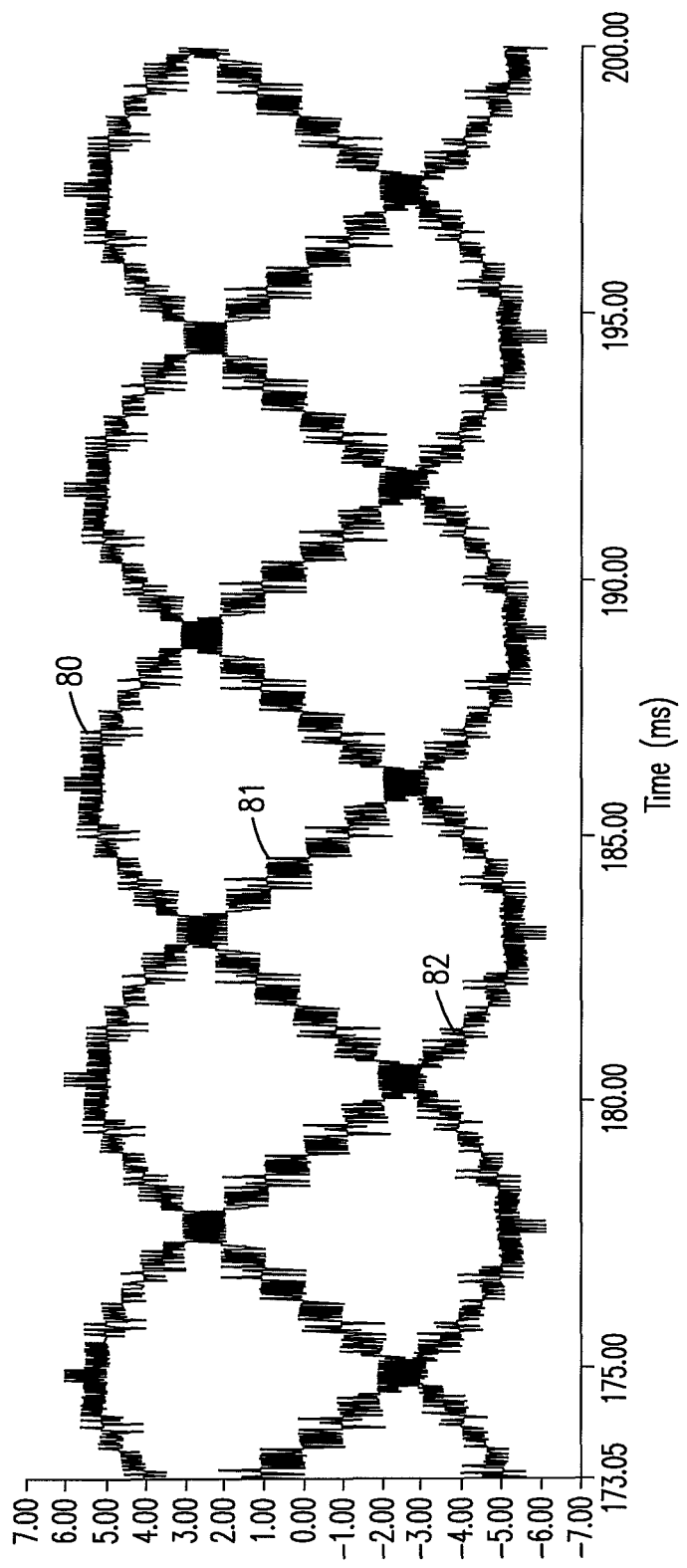
FIG. 15 illustrates simulated line-line voltages for a modular multilevel inverter having a six sub-modules/arm topology with an illustrated modulation method, in accordance with an exemplary embodiment of the present invention.

FIG. 15 illustrates simulated line-line voltages 80, 81, 82 for a modular multilevel inverter having a six sub-modules/arm topology with the illustrated modulation method. As discernable from FIG. 15, the illustrated method provides that if the slope of the arm reference signal waveform is positive, transitions mostly take place from a given level to the next level up, whereas if the slope of the arm reference signal waveform is negative, transitions mostly take place from a given level to the next level down.

Principles of the above described exemplary embodiments may be extended or adapted to several other multilevel converter topologies that generally have, for each phase, a plurality of switching legs including at least one switching device. These may include, for example and without limitation, diode claimed type, capacitor clamped type (with flying capacitors), among others.

While specific embodiments have been described in detail, those of ordinary skill in the art will appreciate that various modifications and alternative to those details could be developed in light of the overall teachings of the disclosure. For example, elements described in association with different embodiments may be combined. Accordingly, the particular arrangements disclosed are meant to be illustrative only and should not be construed as limiting the scope of the claims or disclosure, which are to be given the full breadth of the appended claims, and any and all equivalents thereof. It should be noted that the term "comprising" does not exclude other elements or steps, the use of articles "a" or "an" does not exclude a plurality, and the term "multiple" refers to "a plurality of", i.e., more than one.

What is claimed is:

1. A method for controlling a switching device of a multilevel converter, comprising:
dynamically selecting a carrier signal, and
generating a pulse width modulation signal to effect a switching event of the switching device based on a comparison of the dynamically selected carrier signal with a reference signal,
wherein the carrier signal is dynamically selected from a plurality of carrier signals, each of the plurality of carrier signals corresponding to one of a plurality of contiguous bands into which a range of a waveform of the reference signal is divided, the carrier signals corresponding to different bands having differing waveform shapes, and
wherein the dynamically selected carrier signal corresponds to a band that is instantaneously occupied by the reference signal, the dynamic selection being carried out whereby whenever there is a transition of the reference signal from a first band to a second band, the carrier signals selected for the first band and the second band are dependent on a slope of the waveform of the reference signal at the transition.

2. The method according to claim 1, wherein each of the carrier signals comprises a waveform comprising a first portion corresponding to a rising ramp of the carrier signal, a second portion corresponding to a falling ramp of the carrier signal and at least a third portion wherein the carrier signal is substantially constant.

3. The method according to claim 2, wherein the plurality of carrier signals are divided into a plurality of sets of carrier signals, wherein the carrier signals of the same set have approximately the same frequency and amplitude and different waveform shapes with similar first portions and second portions but differing third portions, each carrier signal of the same set being arranged in one of the plurality of contiguous bands that fully occupy the range of the waveform of the reference signal, and wherein corresponding carrier signals of different sets are shifted in phase from each other.

4. The method according to claim 2, wherein the dynamic selection is carried out whereby the carrier signals selected for both the first band and the second band have their respective first portions synchronized if the slope of the waveform of the reference signal is positive at the transition.

5. The method according to claim 2, wherein the dynamic selection is carried out whereby the carrier signals selected for both the first band and the second band have their respective second portions synchronized if the slope of the waveform of the reference signal is negative at the transition.

6. The method according to claim 1, wherein the waveform of the reference signal has a substantially sinusoidal shape.

7. A method for generating pulse width modulation signals to control a switching leg of a multilevel converter comprising a plurality of switching legs per phase, the method comprising:
dynamically allocating a carrier to each switching leg of the phase, and
generating a pulse width modulation signal to effect a switching event for an individual switching leg based on a comparison of the dynamically allocated carrier with a reference signal,
wherein the dynamically allocated carrier is selected from a plurality of sets of carriers, each carrier having a signal waveform comprising a rising ramp, a falling ramp and a at least one generally flat portion, wherein the carriers of the same set have the same frequency and amplitude and different shapes with similar rising ramps and falling ramps but differing flat portions, being arranged in a plurality of contiguous bands that fully occupy a range of a waveform of the reference signal, wherein corresponding carriers of different sets are shifted in phase from each other,
wherein the dynamic allocation is carried out such that the selected carrier corresponds to the band that is instantaneously occupied by the reference signal, and whereby when there is a transition of the reference signal from a first band to a second band, the carriers selected for the first and second bands have synchronized rising ramps if the second band is at a higher position than the first band, and have synchronized falling ramps if the second band is at a lower position than the first band.

8. The method according to claim 7, wherein the multilevel converter comprises a plurality of power cells connected in series for each phase, each power cell comprising an H-bridge inverter comprising two switching legs, and wherein the inverters of the plurality of power cells are arranged in a cascaded manner with separated DC sources.

9. The method according to claim 8, wherein the total number of carriers for each phase is $(2n)^2$, wherein n is the number of power cells connected in series per phase.

10. The method according to claim 8, wherein the carriers allocated to the two switching legs of the same power cell are displaced in time by an interval Td, where Td=Ts/2n, where Ts is a switching period and n is the number of power cells per phase.

11. The method according to claim 10, wherein the carrier allocated to a first switching leg of one of the power cells and the carrier allocated to a second switching leg of the adjacently cascaded power cell are also displaced in time by the interval Td.

12. The method according to claim 7, wherein the multilevel converter is a modular multilevel converter having two arms per phase, each arm connecting a DC input terminal to an AC output terminal and having an equal number of independently operable power cells connected in series, each power cell comprising a half-bridge inverter with one switching leg.

13. The method according to claim 12, wherein the total number of carriers for each arm is $n^2$, wherein n is the number of power cells per arm.

14. The method according to claim 12, wherein the carriers allocated to the switching legs of adjacently connected cells are displaced in time by an interval Td, where Td=Ts/n, where Ts is a switching period and n is the number of power cells per arm.

15. The method according to claim 7, wherein the dynamic allocation of the carriers is carried out by using a finite state machine to distribute the carriers to the switching legs associated with each phase on a cyclical basis.

16. A method for controlling a multiphase AC power supply, comprising:
supplying power to each phase from a plurality of power cells, wherein each of the power cells has at least one switching leg comprising a semiconductor switching device, and
controlling the voltage output of the individual power cells by controlling switching devices of the respective switching legs by a method according to claim 1.

17. The method according to claim 16, comprising controlling a voltage output of the multiphase power supply to operate a multiphase AC motor connected to the multiphase power supply.

18. A multilevel converter for producing a multiphase AC power supply, comprising:
a plurality of power cells for supplying power to each phase, each power cell comprising at least one switching leg incorporating a semiconductor switch, and a pulse width modulation controller connected to each of the power cells for controlling the voltage output of the respective power cells by controlling a switching event of each of the switching legs by pulse width modulation,
wherein the pulse width modulation controller dynamically selects a carrier for an individual switching leg and generates a switching signal to effect a switching event for the individual switching leg based on a comparison of the dynamically selected carrier with a reference signal,
wherein the pulse width modulation controller executes the dynamic selection of the carrier for the individual switching leg from a plurality of carriers, each of the plurality of carriers corresponding to one of a plurality of contiguous bands into which a range of a waveform of the reference signal is divided, the carriers corresponding to different bands having differing waveform shapes, wherein the dynamically selected carrier corresponds to the band that is instantaneously occupied by the reference signal,
wherein the dynamic selection is executed whereby whenever there is a transition of the reference signal from a first band to a second band, the carrier signals selected for the first band and the second band are dependent on a slope of the waveform of the reference signal at the transition.

19. An electric drive system for use with a multiphase AC load, comprising:
a power source,
a multilevel converter according to claim 18 connected to the power source for supplying power to each phase of the multiphase AC load.

20. The electric drive system of claim 19, wherein the electric drive system comprises a variable speed motor drive.

* * * * *